(12) United States Patent
De Corte et al.

(10) Patent No.: US 7,015,221 B2
(45) Date of Patent: *Mar. 21, 2006

(54) 2,4-DISUBSTITUTED TRIAZINE DERIVATIVES

(75) Inventors: Bart De Corte, Southampton, PA (US); Marc René de Jonge, CA Tilburg (NL); Jan Heeres, Vosselaar (BE); Paul Adriaan Jan Janssen, Vosselaar (BE); Robert W. Kavash, Glenside, PA (US); Lucien Maria Henricus Koymans, Retie (BE); Michael Joseph Kukla, Maple Glen, PA (US); Donald William Ludovici, Quakertown, PA (US); Koen Jeanne Alfons Van Aken, Turnhout (BE)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 10/649,017

(22) Filed: Aug. 27, 2003

(65) Prior Publication Data

US 2005/0277641 A1    Dec. 15, 2005

Related U.S. Application Data

(62) Division of application No. 09/831,808, filed as application No. PCT/EP99/08688 on Nov. 4, 1999, now Pat. No. 6,638,932.

(60) Provisional application No. 60/107,799, filed on Nov. 10, 1998.

(30) Foreign Application Priority Data

Sep. 24, 1999 (EP) .................................. 99203128

(51) Int. Cl.
$C07D\ 251/16$ (2006.01)
$C07D\ 251/18$ (2006.01)
$A61K\ 31/53$ (2006.01)
$A61P\ 31/18$ (2006.01)

(52) U.S. Cl. .................. 514/241; 514/213; 544/194; 544/208; 544/209; 544/213

(58) Field of Classification Search ............... 544/194, 544/208, 209, 213; 514/241, 213
See application file for complete search history.

(56) References Cited

U.S. PATENT DOCUMENTS

| 5,017,466 A | 5/1991 | Kobayashi et al. ......... 430/558 |
| 5,691,364 A | 11/1997 | Buckman et al. ........... 514/341 |
| 6,107,301 A | 8/2000 | Aldrich et al. ............ 514/261.1 |
| 6,200,977 B1 | 3/2001 | Cushing et al. ......... 514/252.14 |
| 6,342,503 B1 | 1/2002 | Aldrich et al. .............. 514/272 |
| 6,528,513 B1 | 3/2003 | Cushing et al. ............. 514/258 |
| 6,638,932 B1 * | 10/2003 | De Corte et al. ........... 514/241 |
| 6,835,726 B1 | 12/2004 | Cushing et al. ............. 514/183 |

FOREIGN PATENT DOCUMENTS

| DE | 2 121 694 | 11/1971 |
| DE | 2226 474 | 2/1973 |
| EP | 0 196 275 | 10/1986 |
| EP | 0 834 507 A1 | 4/1998 |
| FR | 2 099 730 | 3/1972 |

OTHER PUBLICATIONS

Ashley, J.N. et al., "The Search for Chemotherapeutic Amidines. Part XVI Amidinoanilino-1,3,5-triazines and Related Compounds", *Journal of the Chemical Society*, Jan. 1. 1960, 4525-4531, XP 000573907.

Foye, W.O. et al. "Amine Derivative of cyanuric Chloride. IV. Catalytic Hydrogenolysis of Aromatically-bound Chlorine", *J.Am. Pharm. Assoc., Sci Ed.*, 1959, 48, 327-329 (Abstract 1 page).

(Continued)

*Primary Examiner*—Venkataraman Balasubramanian
(74) *Attorney, Agent, or Firm*—Woodcock Washburn LLP

(57) ABSTRACT

This invention concerns the use of the compounds of formula (I)

the N-oxides, the pharmaceutically acceptable addition salts, quaternary amines and the stereochemically isomeric forms thereof, wherein $-a^1=a^2-a^3=a^4-$ forms a phenyl, pyridinyl, pyrimidinyl, pyridazinyl or pyrazinyl with the attached vinyl group; n is 0 to 4; and where possible 5; $R^1$ is hydrogen, aryl, formyl, $C_{1-6}$alkylcarbonyl, $C_{1-6}$alkyl, $C_{1-6}$alkyloxycarbonyl or substituted $C_{1-6}$alkyl; each $R^2$ independently is hydroxy, halo, optionally substituted $C_{1-6}$alkyl, $C_{2-6}$alkenyl or $C_{2-6}$alkynyl, $C_{3-7}$cycloalkyl, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, $-S(=O)_pR^4$, $-NH-S(=O)_pR^4$, $-C(=O)R^4$, $-NHC(=O)H$, $-C(=O)NHNH_2$, $-NHC(=O)R^4$, $-C(=NH)R^4$ or a 5-membered heterocyclic ring; p is 1 or 2; L is optionally substituted $C_{1-10}$alkyl, $C_{2-10}$alkenyl, $C_{2-10}$alkynyl or $C_{3-7}$cycloalkyl; or L is $-X-R^3$ wherein $R^3$ is optionally substituted phenyl, pyridinyl, pyrimidinyl, pyrazinyl or pyridazinyl; X is $-NR^1-$, $-NH-NH-$, $-N=N-$, $-O-$, $-C(=O)-$, $-CHOH-$, $-S-$, $-S(=O)-$ or $-S(=O)_2-$; aryl is optionally substituted phenyl; for the manufacture of a medicine for the treatment of subjects suffering from HIV (Human Immunodeficiency Virus) infection.

10 Claims, No Drawings

OTHER PUBLICATIONS

Rajnani, H.B. et al., "Preparation and Hypnotic Activity of 5'-'2, 4-bis(arylamino)-s-triazin-6-yl!barbituric Acids", *J. Inst. Chem.*, 1978, 50(5), 213-214, XP 002138938.

Burmistrov, S.I. et al., "2,4-Bis(arylamino)-1,3,5,-trazines with Identical Aryl-Amino Groups", *Dzerzhinskii, F.E., Chemical Technlogical Institute,* SU 189 438 1 (Abstract 1 page).

Yuki Yasuo, et al., "Preparation of Poly(Amide-Guanamine) and Poly (Pyromellitimide-Guanamine)", *Nippon Kagaku Kaishi*, 1977, 4, 549-555(Abstract 1 page).

Yuki Yasuo, et al., "Preparation of Poly(Amide-Guanamine) and Poly(Pyromellitimide)", *Department of Fiber and Polymer, Institute of Technology, Japan,* 1977, 4, 549-555, (English Abstract 1 page).

Van Der Plas, H.C. et al., "Ring Transformations in Reactions of Heterocyclic Halogeno Compounds with Nucleophiles (XIV)", *Recl. Trav. Chim. Pays-Bas*, 1969, 88(4), 426-438.

Yuki, Y. et al., "Synthesis and Properties of Polyguanamines from N,N'-Diphenylguanamines and α, w-Dibromoalkanes", *Polymer Journal*, 1996, 28(4), 337-342.

Kobunshi Kagaku, *Department of Fiber and Polymer, Nagoya Institute of Technology*, Dec. 1973, 30(344), 720-726. English Language abstract for previously submitted publication reference #17.

* cited by examiner

2,4-DISUBSTITUTED TRIAZINE DERIVATIVES

CROSS REFERENCE TO RELATED APPLICATIONS

This application is a divisional of application Ser. No. 09/831,808, filed Aug. 2, 2001, now U.S. Pat. No. 6,638,932, which is a National Stage application under 35 U.S.C. § 371 of PCT/EP99/08688 filed Nov. 4, 1999, which claims priority under 35 U.S.C. § 119 from EP 99203128.6, filed Sep. 24, 1999, which claims priority to provisional application Ser. No. 60/107,799, filed Nov. 10, 1998.

The present invention is concerned with 2,4-disubstituted triazine derivatives having HIV replication inhibiting properties. The invention further relates to methods for their preparation and pharmaceutical compositions comprising them. The invention also relates to the use of said compounds in the manufacture of a medicament useful for the treatment of subjects suffering from HIV (Human Immunodeficiency Virus) infection.

EP-0,834,507 discloses substituted diamino 1,3,5-triazine derivatives having HIV replication inhibiting properties. The present compounds differ from the known 1,3,5-triazines by structure and by their improved HIV replication inhibiting properties.

The present invention concerns the use of the compounds of formula

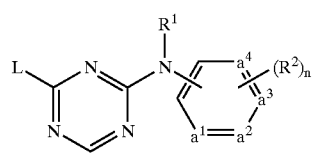

(I)

the N-oxides, pharmaceutically acceptable addition salts, quaternary amines and stereochemically isomeric forms thereof, wherein
-$a^1$=$a^2$-$a^3$=$a^4$- represents a bivalent radical of formula

| | |
|---|---|
| —CH=CH—CH=CH— | (a-1); |
| —N=CH—CH=CH— | (a-2); |
| —N=CH—N=CH— | (a-3); |
| —N=CH—CH=N— | (a-4); |
| —N=N—CH=CH— | (a-5); | n is 0, 1, 2, 3 or 4; and in case -$a^1$=$a^2$-$a^3$=$a^4$- is (a-1), then n may also be 5;

$R^1$ is hydrogen, aryl, formyl, $C_{1-6}$alkylcarbonyl, $C_{1-6}$alkyl, $C_{1-6}$alkyloxycarbonyl, $C_{1-6}$alkyl substituted with formyl, $C_{1-6}$alkylcarbonyl, $C_{1-6}$alkyloxycarbonyl; and each $R^2$ independently is hydroxy, halo, $C_{1-6}$alkyl optionally substituted with cyano or —C(=O)$R^4$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^4$, —NH—S(=O)$_p$$R^4$, —C(=O)$R^4$, —NHC(=O)H, —C(=O)NHNH$_2$, —NHC(=O)$R^4$, —C(=NH)$R^4$ or a radical of formula

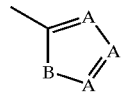

(c)

wherein each A independently is N, CH or CR$^4$;
B is NH, O, S or NR$^4$;
p is 1 or 2; and
$R^4$ is methyl, amino, mono- or dimethylamino or polyhalomethyl;

L is $C_{1-10}$alkyl, $C_{2-10}$alkenyl, $C_{2-10}$alkynyl, $C_{3-7}$cycloalkyl, whereby each of said aliphatic group may be substituted with one or two substituents independently selected from
  $C_{3-7}$cycloalkyl,
  indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl,
  phenyl, pyridinyl, pyrimidinyl, pyrazinyl or pyridazinyl, wherein each of said aromatic rings may optionally be substituted with one, two, three, four or five substituents each independently selected from the substituents defined in $R^2$; or
L is —X—$R^3$ wherein
  $R^3$ is phenyl, pyridinyl, pyrimidinyl, pyrazinyl or pyridazinyl, wherein each of said aromatic rings may optionally be substituted with one, two, three, four or five substituents each independently selected from the substituents defined in $R^2$; and
  X is —NR$^1$—, —NH—NH—, —N=N—, —O—, —C(=O)—, —CHOH—, —S—, —S(=O)— or —S(=O)$_2$—; aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

for the manufacture of a medicine for the treatment of subjects suffering from HIV (Human Immunodeficiency Virus) infection.

This invention also concerns compounds of formula (I') which are defined as compounds of formula (I) wherein the compounds cited in the following references
  Recl. Trav. Chim. Pays-Bas (1969), 88 (4), 426–38.
  Polym. J. (Tokyo) (1996), 28 (4), 337–42.
  J. Inst. Chem. (India) (1978), 50 (5), 213–14.
  Nippon Kagaku Kaishi (1977), Issue 4, 549–55.
  Kobunshi Kagaku (1973), 30 (12), 720–6.
  SU 189438
  DE 2226474
are excluded;
i.e. compounds of formula

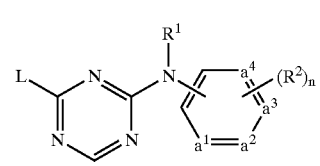

(I')

the N-oxides, addition salts, quaternary amines and stereochemically isomeric forms thereof, wherein the substituents are as defined under formula (I); with the proviso that compounds wherein L is $C_{1-3}$alkyl; $R^1$ is selected from hydrogen, ethyl and methyl; -$a^1$=$a^2$-$a^3$=$a^4$- represents a bivalent radical of formula (a-1); n is 0 or 1 and $R^2$ is selected from fluoro, chloro, methyl, trifluoromethyl, ethyloxy and nitro; or L is —X—$R^3$, X is —NH—; $R^1$ is hydrogen; -$a^1$=$a^2$-$a^3$=$a^4$- represents a bivalent radical of formula (a-1); n is 0 or 1 and $R^2$ is selected from chloro, methyl, methyloxy, cyano, amino and nitro and $R^3$ is phenyl, optionally substituted with one substituent selected from chloro, methyl, methyloxy, cyano, amino and nitro;

and the compounds
N,N'-dipyridinyl-(1,3,5)-triazine-2,4-diamine;
(4-chloro-phenyl)-(4(1-(4-isobutyl-phenyl)-ethyl)-(1,3,5) triazin-2-yl)-amine are not included.

A special group of compounds are compounds of formula (I'), the N-oxides, addition salts, quaternary amines and stereochemically isomeric forms thereof, wherein -$a^1$=$a^2$-$a^3$=$a^4$- represents a bivalent radical of formula

| —CH=CH—CH=CH— | (a-1); |
| —N=CH—CH=CH— | (a-2); |
| —N=CH—N=CH— | (a-3); |
| —N=CH—CH=N— | (a-4); |
| —N=N—CH=CH— | (a-5); | n is 0, 1, 2, 3 or 4; and in case -$a^1$=$a^2$-$a^3$=$a^4$- is (a-1), then n may also be 5;

$R^1$ is hydrogen, aryl, formyl, $C_{1-6}$alkylcarbonyl, $C_{1-6}$alkyl, $C_{1-6}$alkyloxycarbonyl, $C_{1-6}$alkyl substituted with formyl, $C_{1-6}$alkylcarbonyl, $C_{1-6}$alkyloxycarbonyl; and each $R^2$ independently is hydroxy, halo, $C_{1-6}$alkyl optionally substituted with cyano or —C(=O)$R^4$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$$R^4$, —NH—S(=O)$_p$$R^4$, —C(=O)$R^4$, —NHC(=O)H, —C(=O)NHNH$_2$, —NHC(=O)$R^4$, —C(=NH)$R^4$ or a radical of formula

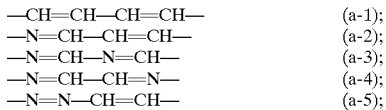

wherein each A independently is N, CH or C$R^4$;
B is NH, O, S or N$R^4$;
p is 1 or 2; and
$R^4$ is methyl, amino, mono- or dimethylamino or polyhalomethyl;
L is $C_{4-10}$alkyl, $C_{2-10}$alkenyl, $C_{2-10}$alkynyl, $C_{3-7}$cycloalkyl, whereby each of said aliphatic group may be substituted with one or two substituents independently selected from $C_{3-7}$cycloalkyl, indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl, phenyl, pyridinyl, pyrimidinyl, pyrazinyl or pyridazinyl, wherein each of said aromatic rings may optionally be substituted with one, two, three, four or five substituents each independently selected from the substituents defined in $R^2$; or L is —X—$R^3$ wherein
$R^3$ is phenyl, pyridinyl, pyrimidinyl, pyrazinyl or pyridazinyl, wherein each of said aromatic rings may optionally be substituted with two, three, four or five substituents each independently selected from the substituents defined in $R^2$; and X is —N$R^1$—, —NH—NH—, —N=N—, —O—, —C(=O)—, —CHOH—, —S—, —S(=O)— or —S(=O)$_2$—;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

and suitably N,N'-dipyridinyl-(1,3,5)-triazine-2,4-diamine is excluded.

Another special group of compounds are those compounds having the formula

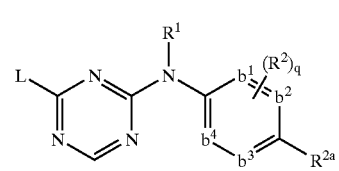

(I-a)

the N-oxides, addition salts, quaternary amines and stereochemically isomeric forms thereof, wherein
-$b^1$=$b^2$-C($R^{2a}$)=$b^3$-$b^4$=represents a bivalent radical of formula

| —CH=CH—C($R^{2a}$)=CH—CH= | (b-1); |
| —N=CH—C($R^{2a}$)=CH—CH= | (b-2); |
| —CH=N—C($R^{2a}$)=CH—CH= | (b-3); |
| —N=CH—C($R^{2a}$)=N—CH= | (b-4); |
| —N=CH—C($R^{2a}$)=CH—N= | (b-5); |
| —CH=N—C($R^{2a}$)=N—CH= | (b-6); |
| —N=N—C($R^{2a}$)=CH—CH= | (b-7); | q is 0, 1, 2; or where possible q is 3 or 4;
$R^1$ is hydrogen, aryl, formyl, $C_{1-6}$alkylcarbonyl, $C_{1-6}$alkyl, $C_{1-6}$alkyloxycarbonyl, $C_{1-6}$alkyl substituted with formyl, $C_{1-6}$alkylcarbonyl, $C_{1-6}$alkyloxycarbonyl;
$R^{2a}$ is cyano; aminocarbonyl; mono- or di(methyl)aminocarbonyl; $C_{1-6}$alkyl substituted with cyano, aminocarbonyl or mono- or di(methyl)aminocarbonyl; $C_{2-6}$alkenyl substituted with cyano; or $C_{2-6}$alkynyl substituted with cyano;
each $R^2$ independently is hydroxy, halo, $C_{1-6}$alkyl optionally substituted with cyano or —C(=O)$R^4$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, —S(=O)$_p$R$^4$, —NH—S(=O)$_p$R$^4$, —C(=O)R$^4$, —NHC(=O)H, —C(=O)NHNH$_2$, —NHC(=O)R$^4$, —C(=NH)R$^4$ or a radical of formula

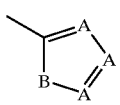

(c)

wherein each A independently is N, CH or CR$^4$;
B is NH, O, S or NR$^4$;
p is 1 or 2; and
R$^6$ is methyl, amino, mono- or dimethylamino or polyhalomethyl;
L is $C_{4-10}$alkyl, $C_{2-10}$alkenyl, $C_{2-10}$alkynyl, $C_{3-7}$cycloalkyl, whereby each of said aliphatic group may be substituted with one of two substituents independently selected from $C_{3-7}$cycloalkyl,
  indolyl or isoindolyl, each optionally substituted with one, two, three or four substituents each independently selected from halo, $C_{1-6}$alkyl, hydroxy, $C_{1-6}$alkyloxy, cyano, aminocarbonyl, nitro, amino, polyhalomethyl, polyhalomethyloxy and $C_{1-6}$alkylcarbonyl,
  phenyl, pyridinyl, pyrimidinyl, pyrazinyl or pyridazinyl, wherein each of said aromatic rings may optionally be substituted with one, two, three, four or five substituents each independently selected from the substituents defined in R$^2$; or
L is —X—R$^3$ wherein
  R$^3$ is phenyl, pyridinyl, pyrimidinyl, pyrazinyl or pyridazinyl, wherein each of said aromatic rings may optionally be substituted with two, three, four or five substituents each independently selected from the substituents defined in R$^2$; and
  X is —NR$^1$—, —NH—NH—, —N=N—, —O—, —C(=O)—, —CHOH—, —S—, —S(=O)— or —S(=O)$_2$—;
aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;
and suitably N,N'-dipyridinyl-(1,3,5)-triazine-2,4-diamine is excluded.

Said special groups of compounds are deemed novel and can be used as a medicine.

The present invention also relates to a method of treating warm-blooded animals suffering from HIV (Human Immunodeficiency Virus) infection. Said method comprises the administration of a therapeutically effective amount of a compound of formula (I), (I') or (I-a) or a N-oxide form, a pharmaceutically acceptable addition salt, a quaternary amine or a stereochemically isomeric form thereof in admixture with a pharmaceutical carrier.

As used in the foregoing definitions and hereinafter $C_{1-3}$alkyl as a group or part of a group encompasses the straight and branched chain saturated hydrocarbon radicals having from 1 to 3 carbon atoms such as, methyl, ethyl and propyl; $C_{1-4}$alkyl encompasses the straight and branched chain saturated hydrocarbon radicals as defined in $C_{1-3}$alkyl as well as butyl; $C_{1-6}$alkyl encompasses the straight and branched chain saturated hydrocarbon radicals as defined in $C_{1-4}$alkyl as well as the higher homologues thereof containing 5 to 6 carbon atoms such as pentyl, hexyl, 2-methylbutyl and the like; $C_{1-10}$alkyl encompasses the straight and branched chain saturated hydrocarbon radicals as defined in $C_{1-6}$alkyl as well as the higher homologues thereof containing 7 to 10 carbon atoms such as, heptyl, octyl, nonyl or decyl; $C_{4-10}$alkyl encompasses the straight and branched chain saturated hydrocarbon radicals as defined above, having from 4 to 10 carbon atoms; $C_{3-7}$cycloalkyl is generic to cyclopropyl, cyclobutyl, cyclopentyl, cyclohexyl and cycloheptyl; $C_{2-6}$alkenyl defines straight and branched chain hydrocarbon radicals containing one double bond and having from 2 to 6 carbon atoms such as, 2-ethenyl, 2-propenyl, 2-butenyl, 2-pentenyl, 3-pentenyl, 3-methyl-2-butenyl, 3-hexenyl and the like; $C_{2-10}$alkenyl encompasses the straight and branched chain hydrocarbon radicals as defined in $C_{2-6}$alkenyl as well as the higher homologues thereof containing 7 to 10 carbon atoms such as 3-heptenyl, 2-octenyl, 2-nonenyl, 2-decenyl and the like, whereby the carbon atom attached to the triazine ring is preferably an aliphatic carbon atom; $C_{2-6}$alkynyl defines straight and branched chain hydrocarbon radicals containing one triple bond and having from 2 to 6 carbon atoms such as, 2-ethynyl, 2-propynyl, 2-butynyl, 2-pentynyl, 3-pentynyl, 3-methyl-2-butynyl, 3-hexynyl and the like; $C_{2-10}$alkynyl encompasses the straight and branched chain hydrocarbon radicals as defined in $C_{2-6}$alkynyl as well as the higher homologues thereof containing 7 to 10 carbon atoms such as 3-heptynyl, 2-octynyl, 2-nonynyl, 2-decynyl and the like, whereby the carbon atom attached to the triazine ring is preferably an aliphatic carbon atom. The term $C_{1-6}$alkyloxy defines straight or branched chain saturated hydrocarbon radicals such as methoxy, ethoxy, propyloxy, butyloxy, pentyloxy, hexyloxy, 1-methylethyloxy, 2-methylpropyloxy, 2-methylbutyloxy and the like; $C_{3-6}$cycloalkyloxy is generic to cyclopropyloxy, cyclobutyloxy, cyclopentyloxy and cyclohexyloxy.

As used herein before, the term (=O) forms a carbonyl moiety when attached to a carbon atom, a sulfoxide group when attached once to a sulfur atom, and a sulfonyl group when attached twice to a sulfur atom.

The term halo is generic to fluoro, chloro, bromo and iodo. As used in the foregoing and hereinafter, polyhalomethyl as a group or part of a group is defined as mono- or polyhalosubstituted methyl, in particular methyl with one or more fluoro atoms, for example, difluoromethyl or trifluoromethyl; polyhalo$C_{1-6}$alkyl as a group or part of a group is defined as mono- or polyhalosubstituted $C_{1-6}$alkyl, for example, the groups defined in halomethyl, 1,1-difluoroethyl and the like. In case more than one halogen atoms are attached to an alkyl group within the definition of polyhalomethyl or polyhalo$C_{1-6}$alkyl, they may be the same or different.

For therapeutic use, salts of the compounds of formula (I), (I') or (I-a) are those wherein the counterion is pharmaceutically acceptable. However, salts of acids and bases which are not pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I), (I') or (I-a) are able to form. The compounds of formula (I), (I') or (I-a) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I), (I') or (I-a) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salts also comprises the hydrates and the solvent addition forms which the compounds of formula (I), (I') or (I-a) are able to form. Examples of such forms are e.g. hydrates, alcoholates and the like.

It will be appreciated that some of the compounds of formula (I), (I') or (I-a) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), (I') or (I-a) and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I), (I') or (I-a) and their N-oxides, addition salts or quaternary amines substantially free, i.e. associated with less than 10%, preferably less than 5%, in particular less than 2% and most preferably less than 1% of the other isomers. In particular, stereogenic centers may have the R- or S-configuration; substituents on bivalent cyclic (partially) saturated radicals may have either the cis- or trans-configuration. Compounds encompassing double bonds can have an E- or Z-stereochemistry at said double bond. Stereochemically isomeric forms of the compounds of formula (I), (I') or (I-a) are obviously intended to be embraced within the scope of this invention.

Some of the compounds of formula (I), (I') or (I-a) may also exist in their tautomeric forms. Such forms although not explicitly indicated in the above formula are intended to be included within the scope of the present invention.

Lines drawn into ring systems from substituents indicate that the bond may be attached to any of the suitable ring atoms.

When any variable (e.g. $R^2$) occurs more than one time in any constituent, each definition is independent.

Whenever used hereinafter, the term "compounds of formula (I)", "compounds of formula (I')", or "compounds of formula (I-a)" is meant to include also the N-oxides, the addition salts, the quaternary amines and all stereoisomeric forms.

An interesting group of compounds are those compounds of formula (I) or (I') wherein one or more of the following conditions are met:

(i) n is 1;
(ii) $-a^1=a^2-a^3=a^4-$ represents a bivalent radical of formula (a-1);
(iii) $R^1$ is hydrogen or alkyl;
(iv) $R^2$ is cyano; aminocarbonyl; mono- or di(methyl)aminocarbonyl; $C_{1-4}$alkyl substituted with cyano, aminocarbonyl or mono- or di(methyl)aminocarbonyl; and more in particular, $R^2$ is on the 4 position relative to the $-NR^1-$ moiety;
i) L is $-X-R^3$ wherein X is preferably $-NR^1-$, $-O-$ or $-S-$, most preferably X is $-NH-$, and $R^3$ is substituted phenyl with $C_{1-6}$alkyl, halogen and cyano as preferred substituents.

Another interesting group of compounds contains those compounds of formula (I-a) wherein one or more of the following restrictions apply:

i) $-b^1=b^2-C(R^{2a})=b^3-b^4=$is a radical of formula (b-1);
ii) q is 0;
iii) $R^{2a}$ is cyano; aminocarbonyl; mono- or di(methyl)aminocarbonyl; $C_{1-6}$alkyl substituted with cyano, aminocarbonyl or mono- or di(methyl)aminocarbonyl, preferably $R^{2a}$ is cyano;
iv) L is $-X-R^3$ wherein X is preferably $-NR^1-$, $-O-$ or $-S-$, most preferably X is $-NH-$, and $R^3$ is substituted phenyl with $C_{1-6}$alkyl, halogen and cyano as preferred substituents.

Preferred compounds are those compounds of formula (I') or (I-a) wherein L is $-X-R^3$ wherein $R^3$ is a disubstituted phenyl group or a trisubstituted phenyl group, each substituent independently selected from chloro, bromo, fluoro, cyano or $C_{1-4}$alkyl.

Compounds of formula (I') wherein L is a radical of formula $-X-R^3$, said compounds are represented by formula (I'-a), can be prepared by reacting an intermediate of formula (II) wherein $W^1$ is a suitable leaving group, for example, a halogen, with an amine derivative of formula (III) in a reaction-inert solvent, for example, tetrahydrofuran, 1,4-dioxane or the like, in the presence of a suitable base such as, triethylamine; and subsequently reacting the thus obtained intermediate of formula (IV) with an intermediate of formula (V) in a reaction-inert solvent such as acetonitrile, 1,4-dioxane or the like, in the presence of a base such as potassium carbonate, sodium hydride, N,N-diisopropyl-ethylamine or the like.

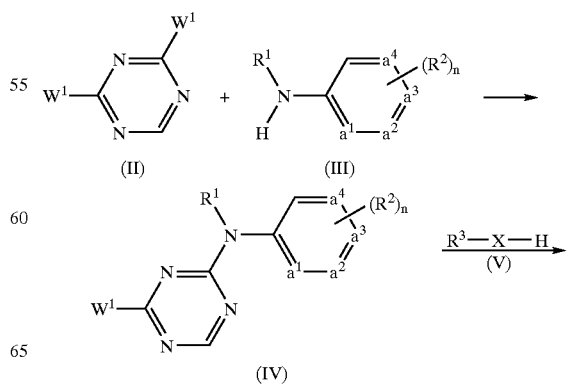

-continued

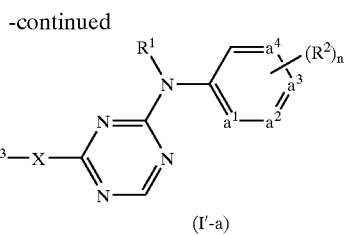

(I'-a)

The order of the above reaction scheme may also be reversed, i.e. first an intermediate of formula (II) may be reacted with an intermediate of formula (V), and then, the resulting intermediate may further be reacted with an amine derivative of formula (III); thus forming a compound of formula (I'-a).

The reaction products may be isolated from the reaction medium and, if necessary, further purified according to methodologies generally known in the art such as, extraction, crystallization, distillation, trituration and chromatography.

Compounds of formula (I') wherein L is an optionally substituted $C_{1-10}$alkyl, $C_{2-10}$alkenyl, $C_{2-10}$alkynyl, $C_{3-7}$cycloalkyl, said L being represented by $L_a$ and said compounds being represented by formula (I'-b), can be prepared by first making a Grignard reagent of an intermediate of formula (VI) wherein $W^2$ is a suitable leaving group such as, a halogen, e.g. bromine, in the presence of magnesium in a reaction-inert solvent such as, diethyl ether, and subsequently reacting said Grignard reagent with an intermediate of formula (VII) wherein $W^1$ is a suitable leaving group such as, a halogen, e.g. chlorine, in a reaction-inert solvent, for example, benzene, thus forming an intermediate of formula (VIII). It may be convenient to perform the above reaction under an inert atmosphere, for instance, argon. Intermediate (VIII) may be isolated from its reaction medium, or may be in situ further reacted with an intermediate of formula (III) in a reaction-inert solvent such as, 1,4-dioxane, and in the presence of a suitable base such as, diisopropylethylamine or the like, thus forming a compound of formula (I'-b).

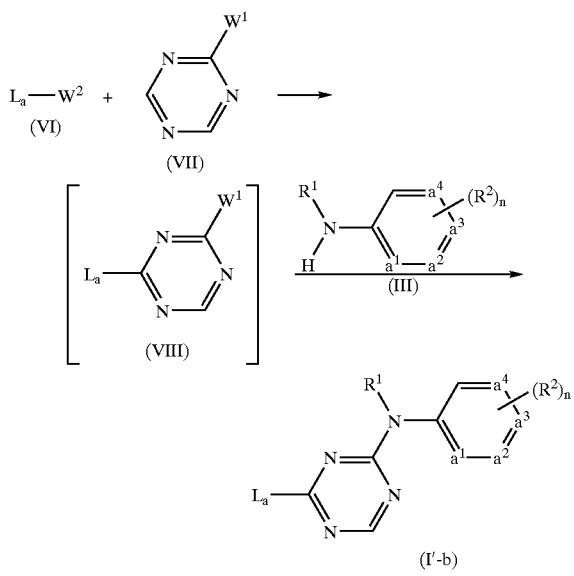

The compounds of formula (I') may further be prepared by converting compounds of formula (I') into each other according to art-known group transformation reactions.

The compounds of formula (I') may be converted to the corresponding N-oxide forms following art-known procedures for converting a trivalent nitrogen into its N-oxide form. Said N-oxidation reaction may generally be carried out by reacting the starting material of formula (I') with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Some of the intermediates as mentioned hereinabove are commercially available or can be prepared according to art-known procedures.

Compounds of formula (I') and some of the intermediates may have one or more stereogenic centers in their structure, present in a R or a S configuration.

The compounds of formula (I') as prepared in the hereinabove described processes may be synthesized as a mixture of stereoisomeric forms, in particular in the form of racemic mixtures of enantiomers which can be separated from one another following art-known resolution procedures. The racemic compounds of formula (I') may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I') involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{1-6}$alkyl or benzyl esters.

The protection and deprotection of functional groups may take place before or after a reaction step.

The use of protecting groups is fully described in 'Protective Groups in Organic Chemistry', edited by J W F McOmie, Plenum Press (1973), and 'Protective Groups in Organic Synthesis' $2^{nd}$ edition, T W Greene & P G M Wutz, Wiley Interscience (1991).

The compounds of formula (I), (I') and (I-a) show antiretroviral properties, in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an everdecreasing number of T4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against HIV-1 strains that have acquired resistance to art-known non-nucleoside reverse transcriptase inhibitors. They also have little or no binding affinity to human α-1 acid glycoprotein.

Due to their antiretroviral properties, particularly their anti-HIV properties, especially their anti-HIV-1-activity, the compounds of formula (I), (I') or (I-a), their N-oxides, addition salts and stereochemically isomeric forms, are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the systemic administration to HIV-infected subjects of an amount effective to combat the conditions associated with HIV and other pathogenic retroviruses, especially HIV-1.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral unit dosage forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Apart from their pharmacological properties, some of the compounds of formula (I') have interesting physicochemical properties. For instance, they have good solubility. To aid solubility of the less soluble compounds of formula (I'), suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxy-propyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles obtainable by melt-extruding a mixture comprising a compound of formula (I') and an appropriate water-soluble polymer and subsequently milling said melt-extruded mixture. Said particles can then be formulated by conventional techniques into pharmaceutical dosage forms such as tablets and capsules.

Said particles consist of a solid dispersion comprising a compound of formula (I') and one or more pharmaceutically acceptable water-soluble polymers. The preferred technique for preparing solid dispersions is the melt-extrusion process comprising the following steps:

a) mixing a compound of formula (I') and an appropriate water-soluble polymer,
b) optionally blending additives with the thus obtained mixture,
c) heating the thus obtained blend until one obtains a homogenous melt,
d) forcing the thus obtained melt through one or more nozzles; and
e) cooling the melt till it solidifies.

The solid dispersion product is milled or ground to particles having a particle size of less than 600 µm, preferably less than 400 µm and most preferably less than 125 µm.

The water-soluble polymers in the particles are polymers that have an apparent viscosity, when dissolved at 20° C. in an aqueous solution at 2% (w/v), of 1 to 5000 mPa.s, more preferably of 1 to 700 mPa.s, and most preferred of 1 to 100 mPa.s. For example, suitable water-soluble polymers include alkylcelluloses, hydroxyalkylcelluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, polysaccharides, polyacrylic acids and the salts thereof, polymethacrylic acids and the salts and esters thereof, methacrylate copolymers, polyvinylalcohol, polyalkylene oxides and copolymers of ethylene oxide and propylene oxide. Preferred water-soluble polymers are Eudragit E® (Röhm GmbH, Germany) and hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy-groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxy-methyl or carboxyethyl.

Of particular utility are the β-cyclodextrin ethers, e.g. dimethyl-α-cyclodextrin as described in Drugs of the Future, Vol. 9, No. 8, p. 577–578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

A more novel type of substituted cyclodextrins is sulfobutylcyclodextrines.

The ratio of compound of formula (I') over cyclodextrin may vary widely. For example ratios of 1/100 to 100/1 may be applied. Interesting ratios of compound of formula (I') over cyclodextrin range from about 1/10 to 10/1. More interesting ratios range from about 1/5 to 5/1.

It may further be convenient to formulate the compounds of formula (I') in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I') but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I') involves a pharmaceutical composition whereby the compounds of formula (I') are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I') and a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I), (I') or (I-a) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

Also, the combination of an antiretroviral compound and a compound of formula (I), (I') or (I-a) can be used as a medicine. Thus, the present invention also relates to a product containing (a) a compound of formula (I), (I'), or (I-a) and (b) another antiretroviral compound, as a combined preparation for simultaneous, separate or sequential use in anti-HIV treatment. The different drugs may be combined in a single preparation together with pharmaceutically acceptable carriers. Said other antiretroviral compounds may be known antiretroviral compounds such as nucleoside reverse transcriptase inhibitors, e.g. zidovudine (3'-azido-3'-deoxythymidine, AZT), didanosine (dideoxy inosine; ddI), zalcitabine (dideoxycytidine, ddC) or lamivudine (3'-thia-2'-3'-dideoxycytidine, 3TC) and the like; non-nucleoside reverse transciptase inhibitors such as suramine, pentamidine, thymopentin, castanospermine, efavirenz, dextran (dextran sulfate), foscarnet-sodium (trisodium phosphono formate), nevirapine (11-cyclopropyl-5,11-dihydro-4-methyl-6H-dipyrido[3,2-b: 2',3'-e][1,4]diazepin-6-one), tacrine (tetrahydroaminoacridine) and the like; compounds of the TIBO (tetrahydroimidazo[4,5,1-jk][1,4]-benzodiazepine-2 (1H)-one and thione)-type e.g. (S)-8-chloro-4,5,6,7-tetrahydro-5-methyl-6-(3-methyl-2-butenyl)imidazo-[4,5,1-jk][1,4]benzodiazepine-2 (1H)-thione; compounds of the α-APA (α-anilino phenyl acetamide) type e.g. α-[(2-nitrophenyl) amino]-2,6-dichlorobenzene-acetamide and the like; TAT-inhibitors, e.g. RO-5-3335 and the like; protease inhibitors e.g. indinavir, ritanovir, saquinovir, ABT-378 and the like; or immunomodulating agents, e.g. levamisole and the like. The compound of formula (I), (I') or (I-a) can also be combined with another compound of formula (I), (I') or (I-a).

The following examples are intended to illustrate the present invention.

Experimental Part

Hereinafter, the term 'RT' means room temperature, 'THF' means tetrahydrofuran and 'EtOAc' means ethyl acetate.

A. Preparation of the Intermediates

EXAMPLE A.1

Starting material 2,4-dichloro-1,3,5-triazine was prepared in 34.8% yield by the method of Synthesis 1981, 907. A solution of 2,4-dichloro-1,3,5-triazine (0.0238 mol) in 1,4-dioxane (120 ml) was prepared with vigorous stirring. 4-Aminobenzonitrile (0.0240 mol) was added in one portion, resulting in a suspension. N,N-bis(1-methylethyl) ethanamine (0.0241 mol) was added. The reaction mixture was stirred at RT for 48 hours. The reaction was concentrated in vacuo to produce a viscous orange syrup which was dissolved with EtOAc and treated with cold 1 M NaOH. The combined aqueous phases were back extracted with EtOAc. The combined organic extracts were dried over MgSO$_4$, filtered and the filtrate was evaporated to give 5.27 g of yellow powder that was subjected to flash chromatography on silica gel (eluent: 100% CH$_2$Cl$_2$ to 90:10 CH$_2$Cl$_2$/Et$_2$O). The pure fractions were collected and the solvent was evaporated to give 3.87 g of off white solid that was recrystallized from CH$_3$CN, filtered off and dried, yielding 3.57 g (64.8%) of 4-[(4-chloro-1,3,5-triazin-2-yl)amino] benzonitrile (Intermediate 1).

B. Preparation of the Final Compounds

EXAMPLE B.1 a) Intermediate (1) (0.00160 mol) was partially dissolved by stirring in 1,4-dioxane (10 ml). Sequentially, 2,4,6-trimethylbenzenamine (0.00164 mol) and N,N-bis(1-methylethyl)ethanamine (0.00164 mol) were added, and the resulting suspension was heated to reflux with stirring. The mixture cleared at 40–50° C. After 4.5 days at reflux, the reaction was cooled to RT, diluted with Et$_2$O, and treated with cold 1 M NaOH. EtOAc was added to dissolve all of the material between the 2 layers. The organic phase was separated and extracted with cold 1 M NaOH. The combined aqueous fractions were washed with EtOAc, adding solid NaOH to adjust the pH to >10. The combined organic phases were dried (MgSO$_4$), filtered and the solvent was evaporated in vacuo to give 0.60 g brown waxy solid. This fraction was purified by flash column chromatography over silica gel (eluent: 100% CH$_2$Cl$_2$ to 80:20 CH$_2$Cl$_2$/Et$_2$O). The pure fractions were collected and the solvent was evaporated to give 0.40 g of white waxy solid that was recrystallized from CH$_3$CN. The precipitate was filtered off and dried, yielding 0.24 g (45.4%) of 4-[[4-[(2,4,6-trimethylphenyl)amino]-1, 3,5-triazin-2-yl]amino]benzonitrile (compound 1).

b) Intermediate (1) (0.00203 mol) and 1,4-dioxane (15 ml) were added to a flask equipped with a condenser. The mixture was stirred vigorously, and 2,6-dibromo-4-(1-methylethyl)benzenamine (0.00205 mol) and N-ethyl-N-(1-methylethyl)-2-propanamine (0.00207 mol) were sequentially added. The reaction was heated to reflux for 5 days (TLC showed some progress). Refluxing was maintained for another day (TLC showed further slow progress). After 12 days total, the reaction was a darker brown with some dark precipitate. The reaction mixture was cooled to room temperature, diluted with EtOAc, treated with cold 1 M NaOH (2×) leaving some brown insoluble solid at the interface. The aqueous phase was pH adjusted to >10 with solid NaOH and was backwashed with EtOAc (2×). The organic phases were combined, dried over MgSO$_4$, filtered and concentrated in vacuo to obtain 0.99 g brown residue. Purification from reverse phase prep HPLC and lyophilization yielded 0.020 g of 4-[[4-[[2,6-dibromo-4-(1-methylethyl)phenyl]amino]-1,3,5-triazin-2-yl]amino]benzonitrile (2.0%, beige fluffy solid) mp. 245–247° C. (compound 8).

c) Intermediate (1) (0.00203 mol) and 1,4-dioxane (15 ml) were added to a flask equipped with a condenser. The mixture was stirred vigorously, and 2,6-dimethyl-4-(1,1-dimethylethyl)benzenamine (0.00203 mol) and N-ethyl-N-(1-methylethyl)-2-propanamine (0.00207 mol) were sequentially added. The reaction was heated to reflux temperature for 5 days (TLC showed high conversion). Refluxing was maintained for another day (TLC showed no further progress). The reaction was cooled to room temperature, diluted with EtOAc, and treated with cold 1 M NaOH. The aqueous phase was pH adjusted to >10 with solid NaOH and backwashed with EtOAc. The organic phases were combined and dried over MgSO$_4$. Concentration afforded 0.90 g tan foam. The residue was purified by flash column chromatography over silica gel (eluent: CH$_2$Cl$_2$ to 90:10 CH$_2$Cl$_2$:Et$_2$O). The pure fractions were collected and the solvent was evaporated to give 0.36 g white solid. This fraction was recrystallized from CH$_3$CN, filtered off and dried. Yielding: 0.28 g of 4-[[4-[[2,6-dimethyl-4-(1,1-dimethylethyl)-phenyl]amino]-1,3,5-triazin-2-yl]amino]benzonitrile (37.0%, white crystalline solid) (compound 9).

EXAMPLE B.2 a) NaH (0.0025 mol) and THF (5 ml) were added to a flask equipped with an addition funnel. A solution of 2,4,6-trimethylphenol (0.00206 mol) in THF (15 ml) was added dropwise with stirring over 15 minutes. The reaction mixture was stirred at room temperature for 45 minutes. Intermediate (1) (0.00203 mol) was added in one portion. The reaction mixture was stirred for 4 days. The reaction was quenched by pouring over ice (75 ml). Upon melting, a minimal amount of precipitate formed. The mixture was treated with $Et_2O$ and EtOAc and the fractions were separated. The pH of the aqueous fraction was adjusted to >10 by treatment with solid NaOH and extracted with EtOAc. The combined organic phases were treated with cold 1 M NaOH. The organic phases were dried over $MgSO_4$. Concentration in vacuo afforded 0.65 g white powder. This fraction was recrystallized from $CH_3CN$, filtered off and dried, yielding 0.50 g (74.4%) of 4-[[4-(2,4,6-trimethylphenoxy)-1,3,5-triazin-2-yl]amino]benzonitrile (compound 2). b) 1-Methyl-2-pyrrolidinone, (5 ml) was added to 3,5-dimethyl-4-hydroxybenzonitrile (0.00258 mol) in a sealed tube reaction flask. The tube was capped with a septum and Ar was introduced via a syringe needle. NaH 60% in oil (0.0030 mol) was added in one portion, and the reaction was stirred for 30 min as the mixture effervesced and became an orange solution. A suspension of intermediate (1) (0.00173 mol) in 1,4-dioxane (15 ml) was added and the flask was sealed and then heated to 160–170° C. for 64 hours. The reaction mixture was cooled to room temperature and analyzed by HPLC/MS which showed some desired product formation with complete consumption of intermediate (1). The sample was poured into ice (±200 ml) and allowed to melt. A precipitate formed and the mixture was cooled in the refrigerator. Collected 0.31 g brown powder by suction filtration which was subjected to purification through preparative HPLC. Upon lyophilization, obtained 0.02 g of 4-[[4-[(4-cyanophenyl)amino]-1,3,5-triazin-2-yl]oxy]-3,5-dimethylbenzonitrile beige flaky solid (3.4%); mp. 248–250° C. (compound 11).

EXAMPLE B.3

Intermediate (1) (0.00203 mol) and 1,4-dioxane (15 ml) were added to a flask and stirred. Sequentially, 2,4,6-trimethylbenzenethiol (0.00204 mol) and N,N-bis(1-methylethyl)ethanamine (0.00207 mol) were added and stirred at ambient temperature. After stirring for one hour, THF (10 ml) was added. The reaction mixture was heated to reflux for 64 hours and cooled to RT. The reaction mixture was diluted with EtOAc and treated with cold 1 M NaOH. The aqueous phase was extracted with EtOAc while maintaining the pH >10 with the addition of solid NaOH. The combined organic phases were dried over $MgSO_4$ and concentrated to afford 0.75 g yellow powder. The residue was crystallized from $CH_3CN$, filtered off and dried, yielding 0.64 g (90.7%) of 4-[[4-[(2,4,6-trimethylphenyl)thio]-1,3,5-triazin-2-yl]amino]benzonitrile (compound 3).

Table 1 lists the compounds of formula (I') which were prepared according to one of the above examples.

TABLE 1

| Comp. No. | Ex. No. | X | $R^a$ | $R^b$ | $R^c$ | Physical Data |
|---|---|---|---|---|---|---|
| 1 | B1a | —NH— | $CH_3$ | $CH_3$ | $CH_3$ | mp. 248–249° C. |
| 2 | B2a | —O— | $CH_3$ | $CH_3$ | $CH_3$ | mp. 220–221° C. |
| 3 | B2a | —O— | $CH_3$ | Br | Cl | mp. 221–222° C. |
| 4 | B3 | —S— | $CH_3$ | $CH_3$ | $CH_3$ | mp. 256–257° C. |
| 5 | B2a | —O— | Br | $CH_3$ | Br | mp. 255–257° C. |
| 6 | B1a | —NH— | Br | $CH_3$ | Br | mp. 285–286° C. |
| 7 | B1a | —NH— | $CH_3$ | Br | $CH_3$ | mp. 248–249° C. |
| 8 | B1b | —NH— | Br | $CH(CH_3)_2$ | Br | mp. 245–247° C. |
| 9 | B1c | —NH | $CH_3$ | $C(CH_3)_3$ | $CH_3$ | mp. 249–250° C. |
| 10 | B1c | —NH | $CH_3$ | CN | $CH_3$ | mp. 252–254° C. |
| 11 | B2b | —O— | $CH_3$ | CN | $CH_3$ | mp. 248–250° C. |

C. Pharmacological Example

EXAMPLE C.1

A rapid, sensitive and automated assay procedure was used for the in vitro evaluation of anti-HIV agents. An HIV-1 transformed T4-cell line, MT-4, which was previously shown (Koyanagi et al., *Int. J. Cancer*, 36, 445–451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MTT). The 50% cytotoxic concentration ($CC_{50}$ in $\mu M$) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%,}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration ($IC_{50}$ in $\mu M$). The ratio of $CC_{50}$ to $IC_{50}$ was defined as the selectivity index (SI). The compounds of formula (I') were shown to inhibit HIV-1 effectively. Particular $IC_{50}$, $CC_{50}$ and SI values are listed in Table 3 hereinbelow.

TABLE 2

| Co. No. | IC$_{50}$ ($\mu$M) | CC$_{50}$ ($\mu$M) | SI |
|---|---|---|---|
| 1 | 0.0004 | 9.1 | 22722 |
| 2 | 0.0006 | >100 | >166666 |
| 3 | 0.0011 | 56.2 | 53536 |
| 4 | 0.0022 | >100 | >46511 |
| 5 | 0.0016 | 10.1 | 6452 |
| 6 | 0.0005 | 1.0 | 1901 |
| 7 | 0.0007 | 27.8 | 39722 |

What is claimed is:

1. A compound of formula

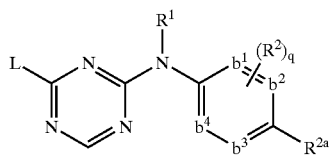

(I-a)

or a N-oxide, a pharmaceutically acceptable salt, or a stereochemically isomeric form thereof, wherein -b$^1$=b$^2$-C(R$^{2a}$)=b$^3$-b$^4$=represents a bivalent radical of formula

| | |
|---|---|
| —CH=CH—C(R$^{2a}$)=CH—CH= | (b-1); |
| —N=CH—C(R$^{2a}$)=CH—CH= | (b-2); |
| —CH=N—C(R$^{2a}$)=CH—CH= | (b-3); |
| —N=CH—C(R$^{2a}$)=N—CH= | (b-4); |
| —N=CH—C(R$^{2a}$)=CH—N= | (b-5); |
| —CH=N—C(R$^{2a}$)=N—CH= | (b-6); or |
| —N=N—C(R$^{2a}$)=CH—CH= | (b-7); | q is 0, 1, 2, 3 or 4;
R$^1$ is hydrogen, aryl, formyl, C$_{1-6}$alkylcarbonyl, C$_{1-6}$alkyl, C$_{1-6}$alkyloxycarbonyl, C$_{1-6}$alkyl substituted with formyl, C$_{1-6}$alkylcarbonyl, or C$_{1-6}$alkyloxycarbonyl;
R$^{2a}$ is cyano; aminocarbonyl; mono- or di(methyl)aminocarbonyl; C$_{1-6}$alkyl substituted with cyano, aminocarbonyl or mono- or di(methyl)aminocarbonyl; C$_{2-6}$alkenyl substituted with cyano; or C$_{2-6}$alkynyl substituted with cyano;
each R$^2$ independently is hydroxy, halo, C$_{1-6}$alkyl optionally substituted with cyano or —C(=O)R$^4$, C$_{3-7}$cycloalkyl, C$_{2-6}$alkenyl optionally substituted with one or more halogen atoms or cyano, C$_{2-6}$alkynyl optionally substituted with one or more halogen atoms or cyano, C$_{1-6}$alkyloxy, C$_{1-6}$alkyloxycarbonyl, carboxyl, cyano, nitro, amino, mono- or di(C$_{1-6}$alkyl)amino, polyhalomethyl, polyhalomethyloxy, polyhalomethylthio, —S(=O)$_p$R$^4$, —NH—S(=O)$_p$R$^4$, —C(=O)R$^4$, —NHC(=O)H, —C(=O)NHNH$_2$, —NHC(=O)R$^4$, —C(=NH)R$^4$ or a radical of formula

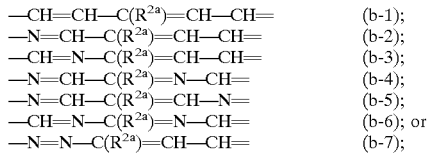

(c)

wherein each A independently is N, CH or CR$^4$;
B is NH, O, S or NR$^4$;
p is 1 or 2; and
R$^4$ is methyl, amino, mono- or dimethylamino or polyhalomethyl;
L is C$_{4-10}$alkyl, C$_{2-10}$alkenyl, C$_{2-10}$alkynyl, or C$_{3-7}$cycloalkyl, whereby each of said aliphatic groups is optionally substituted with one or two substituents independently selected from
(i) C$_{3-7}$cycloalkyl,
(ii) indolyl or isoindolyl, each optionally substituted with one, two, three or four substituents each independently selected from halo, C$_{1-6}$alkyl, hydroxy, C$_{1-6}$alkyloxy, cyano, aminocarbonyl, nitro, amino, polyhalomethyl, polyhalomethyloxy or C$_{1-6}$alkylcarbonyl,
(iii) phenyl, pyridinyl, pyrimidinyl pyrazinyl or pyridazinyl, wherein each of said aromatic rings is optionally substituted with one, two, three, four or five substituents each independently selected from the substituents defined in R$^2$; or
L is —X—R$^3$ wherein
R$^3$ is phenyl, pyridinyl, pyrimidinyl, pyrazinyl or pyridazinyl, wherein each of said aromatic rings is optionally substituted with two, three, four or five substituents each independently selected from the substituents defined in R$^2$; and
X is —NR$^1$—, —NH—NH—, —N=N—, —O—, —C(=O)—, —CHOH—, —S—, —S(=O)— or —S(=O)$_2$—;
aryl is phenyl or phenyl substituted with one, two, three, four or five substituents each independently selected from halo, C$_{1-6}$alkyl, C$_{3-7}$cycloalkyl, C$_{1-6}$alkyloxy, cyano, nitro, polyhaloC$_{1-6}$alkyl or polyhaloC$_{1-6}$alkyloxy.

2. A compound as claimed in claim 1 wherein L is —X—R$^3$, —X— is —O— or —NH— and R$^3$ is phenyl substituted with two or three substituents each independently selected from chloro, bromo, cyano or methyl.

3. A compound as claimed in claim 1 wherein R$^{2a}$ is cyano, aminocarbonyl, mono- or di(methyl)aminocarbonyl, C$_{1-6}$alkyl substituted with cyano, aminocarbonyl or mono- or di(methyl)aminocarbonyl.

4. A method of treating a subject suffering from Human Immunodeficiency Virus (HIV) infection, comprising administering a therapeutically effective amount of a compound of claim 1 to said subject.

5. A pharmaceutical composition comprising a pharmaceutically acceptable carrier and a therapeutically effective amount of compound as claimed in claim 1.

6. A process for preparing a pharmaceutical composition as claimed in claim 5 comprising mixing a therapeutically effective amount of said compound with a pharmaceutically acceptable carrier.

7. The combination of a compound as defined in claim 1 and another antiretroviral compound.

8. A pharmaceutical composition comprising a pharmaceutically acceptable carrier and as active ingredients (a) a compound as defined in claim 1, and (b) another antiretroviral compound.

9. The method of claim 4 further comprising administering a therapeutically effective amount of another antiretroviral compound to said subject.

10. The method of claim 9 wherein said compound and said another antiretroviral compound are administered simultaneously, separately, or sequentially to said subject.

* * * * *